United States Patent [19]

Drehman

[11] 4,000,206
[45] Dec. 28, 1976

[54] PROCESS FOR THE PRODUCTION OF BENZENE, CYCLOHEXANE AND MOTOR FUEL FROM A $C_6$ HYDROCARBON STREAM

[75] Inventor: Lewis E. Drehman, Bartlesville, Okla.

[73] Assignee: Phillips Petroleum Company, Bartlesville, Okla.

[22] Filed: Oct. 16, 1975

[21] Appl. No.: 623,121

[52] U.S. Cl. .................. 260/666 P; 208/57; 208/93; 208/138; 260/668 A; 260/673; 260/674 H
[51] Int. Cl.² ................ C07C 13/18; C07C 15/04
[58] Field of Search ............ 260/666 P, 673, 674, 260/668; 208/93, 138

[56] References Cited
UNITED STATES PATENTS

| | | | |
|---|---|---|---|
| 2,953,606 | 9/1960 | Deau et al. | 260/666 |
| 3,009,002 | 11/1961 | Kron | 260/667 |
| 3,150,195 | 9/1964 | Findlay | 260/666 |
| 3,211,797 | 10/1965 | Houston | 260/668 |
| 3,250,816 | 5/1966 | Waldby | 260/666 |
| 3,644,196 | 2/1972 | Lawson | 260/666 P |
| 3,670,044 | 6/1972 | Drehmau et al. | 208/138 |
| 3,844,935 | 10/1974 | Drehmau et al. | 208/138 |

*Primary Examiner*—Veronica O'Keefe

[57] ABSTRACT

A $C_6$ hydrocarbon stream is converted to benzene, cyclohexane and a motor fuel blending stock by a combination of steps comprising fractionation, hydrogenation and isomerization of the fractions boiling in the isohexanes range and above the n-hexane range, and reforming of the fraction boiling in the n-hexane range and separately recovering a motor fuel blending stock, cyclohexane and benzene as products of the process.

10 Claims, 1 Drawing Figure

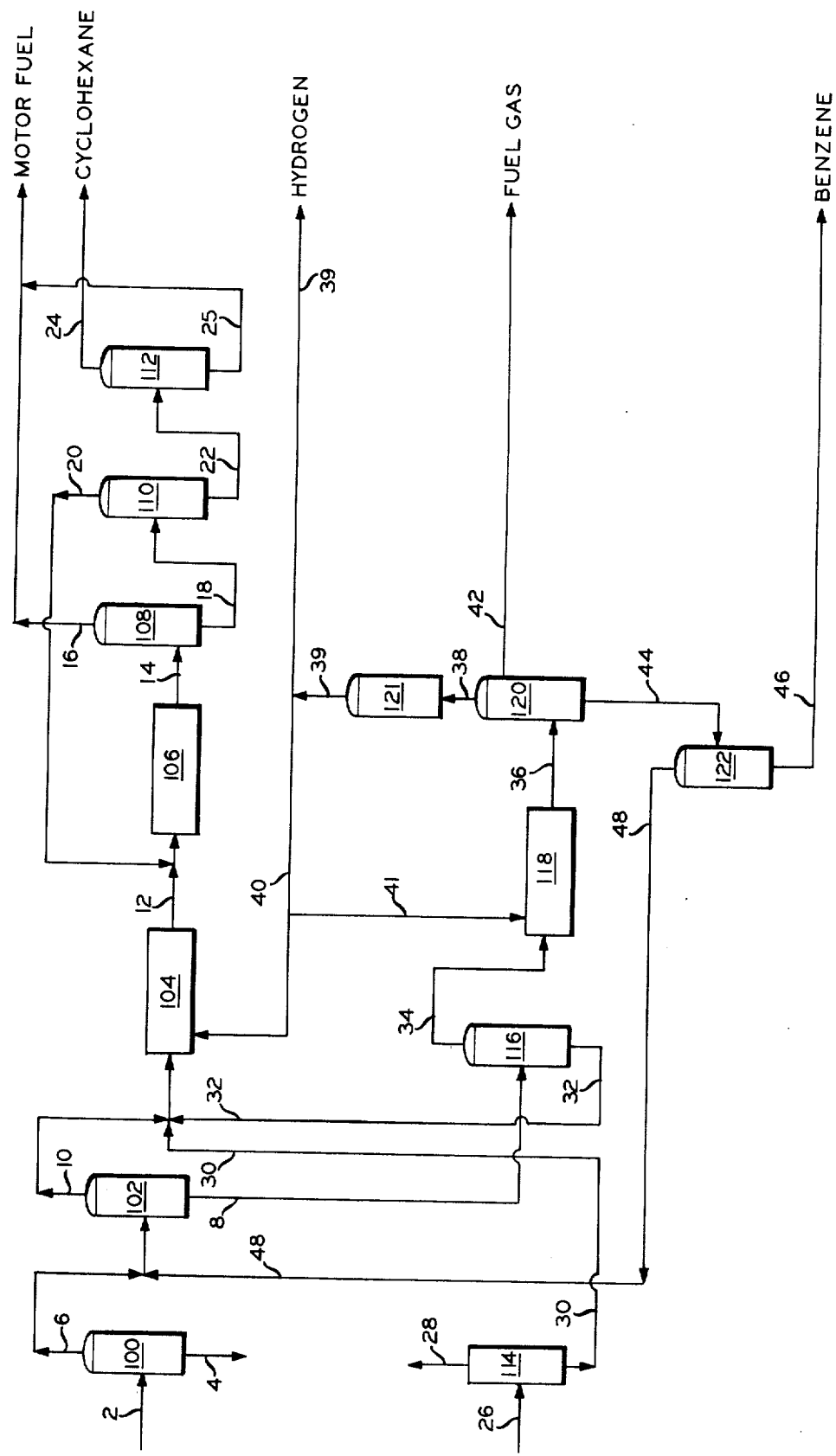

PROCESS FOR THE PRODUCTION OF BENZENE, CYCLOHEXANE AND MOTOR FUEL FROM A $C_6$ HYDROCARBON STREAM

This invention relates to a process for the conversion of hydrocarbons.

Various hydrocarbon fractions of petroleum and natural gas contain large amounts of naphthenic compounds and normal and branched paraffins. Many of these compounds are relatively useless in their original form; however, they can be converted to valuable materials which are useful in motor fuels or as starting materials in chemical processes. Thus, for example, normal hexane and methylpentanes which have low octane numbers can be converted to dimethylbutanes which have high octane numbers and are valuable components of motor fuels. Also, for example, methylcyclopentane can be converted to cyclohexane which is a starting material in the manufacture of nylon.

It is an object of this invention to provide an improved process for the conversion of hydrocarbons.

It is another object to provide a process for the production of benzene, cyclohexane and an isohexanes concentrate.

Other objects, aspects and advantages of the present invention will be apparent to those skilled in the art from a study of the detailed description, appended claims and the drawing which is a schematic diagram of the process of this invention.

In accordance with the present invention there is provided an improved process for the production of benzene, cyclohexane and motor fuel from a $C_6$ hydrocarbon stream which comprises separating the $C_6$ stream to produce a stream boiling in the isohexanes range and a stream boiling above the isohexanes range, separating the stream boiling above the isohexanes range to produce a stream boiling in the n-hexane range and a stream boiling above the n-hexane range, combining the stream boiling above the n-hexane range with the previously separated stream boiling in the isohexanes range, hydrogenating this combined stream, isomerizing the hydrogenated stream, reforming the stream boiling in the n-hexane range and separately recovering the isohexanes concentrate, cyclohexane and benzene as products of the process.

More particularly, in accordance with the present invention, a feedstock selected from the group consisting of natural gas liquids and crude oil is treated by conventional refining techniques to obtain a liquid fraction in which the major constituent consists essentially of hydrocarbons having six carbon atoms, namely isohexanes, n-hexane, methylcyclopentane, cyclohexane and benzene. The fraction consisting essentially of hydrocarbons having six carbon atoms is fractionated to obtain a fraction comprising hydrocarbons having six carbon atoms and boiling in the isohexane range; and a fraction comprising hydrocarbons having six carbon atoms and boiling above the isohexanes range. The fraction comprising hydrocarbons having six carbon atoms and boiling above the isohexanes range is separated to obtain a fraction comprising hydrocarbons having six carbon atoms and boiling in the n-hexane range and a fraction comprising hydrocarbons having six carbon atoms and boiling above the n-hexane range. The fraction comprising hydrocarbons having six carbon atoms and boiling in the n-hexane range is reformed under reforming conditions in the presence of a particular catalyst system and steam to produce a reformate from which benzene is thereafter separated. The fraction comprising hydrocarbons having six carbon atoms and boiling above the n-hexane range is combined with the previously separated fraction comprising hydrocarbons having six carbon atoms and boiling in the isohexanes range. The resulting combined stream is hydrogenated to provide an effluent comprising saturated hydrocarbons having six carbon atoms, which effluent is isomerized to convert methylcyclopentane to cyclohexane. The isomerization effluent is separated to obtain an isohexanes concentrate and a fraction comprising cyclohexane. The fraction comprising cyclohexane is separated to obtain a cyclohexane concentrate.

The several treatment and fractionation zones, including the hydrogenation, isomerization and reforming zones are known in the art and are operated at conventional conditions with known catalysts, where such materials are employed. Such zones and conditions will not be discussed herein in any detail.

In an embodiment of the present invention the reforming operation is effected in the presence of a particular steam-stable catalyst system. Thus, in accordance with the present invention, the n-hexane-containing feed to the reforming zone is contacted under reforming conditions in the presence of steam and a steam-stable catalyst selected from the group consisting of at least one Group VIII metal or metal compound capable of reduction in combination with a tin-modified support selected from the group consisting of Group II aluminates, particularly Group II aluminate spinels, preferably zinc aluminate spinel, and mixtures thereof. The reformate is separated by conventional means to provide a benzene concentrate.

The Group VIII metals include nickel, platinum, palladium, iridium and osmium, including compounds of such metals which are capable of reduction, e.g., nickel nitrate, and including mixtures thereof. A presently preferred Group VIII metal is platinum.

The Group VIII metal content of the catalyst should be in the approximate range of 0.1 to 5 weight percent, preferably 0.1 to 1 weight percent, of the support.

The tin-modified support material should contain from about 0.01 to about 5 weight percent tin, based on the weight of finished support, preferably from about 0.1 to about 2 weight percent. The tin compound can be added to the support material in a conventional manner such as by deposition from solution, ball mill mixing, volatilization, plasma spraying and the like. The tin compound is incorporated with the support material prior to calcination of the support. Regardless of the manner of preparation, the tin compound must be capable of being converted to either the stannous or stannic oxide form, or to tin metal, per se, as by conversion during calcination. Among the tin compounds which can be employed as the source for the tin or tin oxide in the support compositions are the halides, nitrates, oxalates, acetates, propionates, tartarates, hydroxides, and the like. Subsequent to incorporation of the tin, the resulting intimate mixture is calcined for about 1 to 100 hours at temperatures in the approximate range of 600° to 2500° F (316°–1371° C).

In addition to the Group VIII metals, the catalyst composition can include activating components such as alkali metal and alkaline earth metal compounds as well as tin, germanium and lead. The amount of alkali metal or alkaline earth metal is generally within the approximate range of 0.5 to 10 weight percent of the total catalyst. The amount of additional tin will be within the approximate range of 0.1 to 5 weight percent; the amount of germanium or lead will be within the approximate range of 0.1 to 5 weight percent of the total catalyst.

The Group VIII metal compound and, optionally, the adjuvant such as alkali metal, alkaline earth metal, tin, lead or germanium, are applied to the tin-modified support sequentially or simultaneously in a single impregnation procedure. After impregnation the catalyst composites are dried and can be calcined, if desired.

The reforming operation of this invention is carried out at temperatures in the approximate range of 900° to 1200° F (482°–649° C) preferably from 1020° to 1080° F (549° to 582° C). Pressures are generally in the approximate range of 50 to 200 psig (0.345 to 1.379 MPa), and the space velocity is in the approximate range of 0.5 to 3 liquid volumes of feedstock per volume of feedstock per volume of catalyst per hour (LHSV). The reforming in accordance with the present invention is carried out in the vapor phase in the absence of oxygen at molar ratios of steam to feedstock in the approximate range of 5:1 to 30:1. Optionally, the reforming can be carried out in the presence of up to about 2 moles of hydrogen per mole of feed.

The hydrogenation operation can comprise any suitable process and apparatus known in the art for hydrogenation of aromatics and olefinic compounds to the corresponding saturated compounds. Any suitable catalyst for hydrogenation can be employed. Examples of such catalysts are nickel on alumina and nickel on Kieselguhr. One presently preferred catalyst is a nickel on Kieselguhr catalyst containing from about 20 to about 55 weight percent nickel. Typical operating conditions for such hydrogenation includes a temperature within the approximate range of 370° to 550° F (188°–288° C), a pressure within the approximate range of 400 to 600 psig (2.758 to 4.137 MPa), a liquid hourly space velocity (LHSV) within the approximate range of 1 to 3, and a hydrogen to hydrogenatable feedstock mole ratio within the approximate range of 1 to 15.

The isomerization operation can comprise any suitable process and apparatus known in the art for isomerizing methylcyclopentane to cyclohexane and n-hexane to isohexanes. Any suitable catalyst can be employed for such isomerization. In one presently preferred process the catalyst employed is an aluminum chloride-hydrocarbon complex catalyst, promoted with anhydrous hydrogen chloride. Typical operating conditions for such isomerization include a temperature within the approximate range of 100° to 200° F (38° to 93° C), a pressure within the approximate range of 100 to 600 psig (0.68 to 4.14 MPa), an HCl content within the range of 2 to 10 mole percent of the feed and an LHSV in the approximate range of 0.5 to 3.

Referring now to the drawing, a feedstream comprising $C_6$ hydrocarbons with some $C_7$ hydrocarbons is introduced through line 2 to feedstock processing zone 100 wherein the feedstock is separated into a fraction consisting essentially of liquid hydrocarbons having six carbon atoms, with some $C_5$ and $C_7$ hydrocarbons also present, and a fraction comprising $C_7$ and heavier hydrocarbons. The $C_7$ and heavier hydrocarbon fraction is withdrawn from processing zone 100 through line 4 and passed to further processing, not shown. The fraction consisting essentially of $C_6$ hydrocarbons is withdrawn from processing zone 100 through line 6 and passed to fractionation zone 102. In fractionation zone 102 the stream consisting essentially of $C_6$ hydrocarbons is separated into an overhead stream comprising hydrocarbons having a boiling point in the isohexanes range, i.e., isohexanes and lower boiling components, and a bottoms stream having a boiling point above the isohexanes ranges, i.e., n-hexane and higher boiling components. The bottoms fraction comprising $C_6$ hydrocarbons having a boiling point above the isohexanes range is withdrawn from fractionation zone 102 through line 8 and passed to fractionation zone 116, as hereinafter described. The overhead stream comprising hydrocarbons boiling in the isohexanes range is withdrawn from fractionation zone 102 through line 10 and passed to hydrogenation zone 104. The effluent from the hydrogenation zone 104 is passed by line 12 to isomerization zone 106. The effluent from the isomerization zone 106 is passed by line 14 to fractionation zone 108 where the stream is separated into an isohexanes concentrate enriched in high octane components, which is withdrawn from fractionation zone 108 through product line 16, and a fraction comprising cyclohexane, isohexanes, methylcyclopentane and n-hexane, which is withdrawn from fractionation zone 108 through line 18 and passed to fractionation zone 110. In fractionation zone 110 the fraction comprising cyclohexane, isohexanes, methylcyclopentane and n-hexane is separated into an overhead fraction comprising isohexanes, methylcyclopentane and n-hexane, and a bottoms fraction consisting essentially of cyclohexane together with a minor amount of $C_7$ and heavier hydrocarbons. The overhead fraction comprising isohexanes, methylcyclopentane and n-hexane is withdrawn from fractionation zone 110 and passed through line 20 to isomerization zone 106. The bottoms fraction consisting essentially of cyclohexane is withdrawn from fractionation zone 110 and passed through line 22 to fractionation zone 112 wherein it is separated into an overhead fraction consisting essentially of cyclohexane and a bottoms fraction comprising $C_7$ and heavier hydrocarbons. The overhead fraction consisting essentially of cyclohexane is withdrawn from fractionation zone 112 through product line 24. The bottoms fraction comprising $C_7$ and heavier hydrocarbons is withdrawn from fractionation zone 112 through line 25 and combined with the isohexane concentrate in product line 16, as shown, or it can be passed to further processing, not shown.

Optionally, a second feedstream comprising $C_4$–$C_6$ hydrocarbons is introduced through line 26 to feedstock processing zone 114 wherein the feedstock is separated into an overhead fraction comprising $C_5$ and lighter components and a bottoms fraction consisting essentially of $C_6$ hydrocarbons. The overhead fraction comprising $C_5$ and lighter hydrocarbons is withdrawn from processing zone 114 through line 28 and passed to further processing, not shown. The bottoms fraction consisting essentially of $C_6$ hydrocarbons is withdrawn from processing zone 114 and passed through line 30 to the hydrogenation zone 104.

The bottoms fraction comprising $C_6$ hydrocarbons having a boiling point above the isohexanes range is withdrawn from fractionation zone 102 and passed through line 8 to fractionation zone 116, wherein it is separated into an overhead fraction consisting essentially of n-hexane with minor amounts of hexenes, isohexanes, methylcyclopentane and benzene, and a bottoms fraction consisting essentially of methylcyclopentane and n-hexane with minor amounts of benzene and cyclohexane. The bottoms fraction is withdrawn from fractionation zone 116 and passed through line 32 to hydrogenation zone 104. The overhead fraction consisting essentially of n-hexane is withdrawn from fractionation zone 116 and passed through line 34 to reforming zone 118.

The effluent from the reforming zone 118 is passed through line 36 to separation zone 120 wherein the reforming effluent is separated into a hydrogen fraction, a fuel gas fraction and a $C_6$ hydrocarbon fraction consisting essentially of benzene, isohexanes, n-hexenes and n-hexane. The hydrogen fraction is withdrawn from separation zone 120 through line 38 and passed to purification zone 121 wherein the hydrogen is separated from carbonaceous gases such as carbon dioxide, methane, ethane and the like. Substantially pure hydrogen is withdrawn from purification zone 121 through line 39. At least a portion of the hydrogen in line 39 is passed through line 40 to hydrogenation zone 104. If it is desired to conduct the reforming operation in the presence of hydrogen, a portion of the hydrogen in line 40 can be withdrawn therefrom and passed through line 41 to reforming zone 118. The fuel gas fraction is withdrawn from separation zone 120 through line 42. The $C_6$ hydrocarbon fraction is withdrawn from separation zone 120 and passed through line 44 to separation zone 122 wherein the benzene is separated from the remaining $C_6$ hydrocarbons. The benzene is withdrawn from separation zone 122 through product line 46. The remaining $C_6$ hydrocarbons, consisting essentially of n-hexane, n-hexenes and isohexanes are withdrawn from separation zone 122 and passed through line 48 to fractionation zone 102.

The following example is illustrative of the invention:

EXAMPLE

The principal liquid streams are calculated, based on experimental data, to have the following compositions in terms of volume percent:

Table I

| | Composition of Liquid Streams in Volume Percent | | | | | | | | | |
|---|---|---|---|---|---|---|---|---|---|---|
| | Stream | | | | | | | | | |
| | Overhead 6 | Recycle 48 | Bottoms 30 | Overhead 10 | Recycle 32 | Recycle 20 | Feed to Reformer 34 | Isohexanes Concentrate 16 | Cyclo-hexane 24 | Benzene 46 |
| $C_3$'s + $C_4$'s | — | — | — | — | — | — | — | 0.1 | — | — |
| $C_5$'s | 5.0 | — | 12.2 | 15.5 | — | — | — | 12.4 | — | — |
| 2,2-dimethylbutane | 0.6 | — | 3.5 | 1.9 | — | — | — | 23.4 | — | — |
| 2,3-dimethylbutane | 1.3 | — | 8.0 | 4.0 | — | 3.5 | — | 12.4 | — | — |
| 2-methylpentane | 11.4 | 1.2[a] | 53.8 | 35.3[a] | — | 36.3 | 0.5 | 45.2 | — | — |
| 3-methylpentane | 10.4 | 17.2[a] | 17.6 | 32.0[a] | — | 30.1 | 7.1[a] | 6.5 | — | — |
| n-hexane | 48.8 | 76.2[a] | 3.9 | 10.9 | 23.4[a] | 20.7 | 87.9[a] | 0.1 | 0.1 | 1.9[a] |
| Methylcyclopentane | 18.5 | 2.4[a] | 1.1 | — | 67.0[a] | 8.8 | 1.4[a] | — | 0.3 | 0.1[a] |
| Benzene | 2.3 | 2.9 | — | 0.3 | 3.2 | — | 3.1 | — | — | 98.0 |
| Cyclohexane | 1.4 | — | — | — | 5.4 | 0.6 | — | — | 98.6 | — |
| $C_7$+ | 0.3 | — | — | — | 1.1 | — | — | — | 1.1 | — |
| Volume Per Day | | | | | | | | | | |
| Thousands of Gallons | 370.00 | 101.86 | 99.6 | 118.82 | 100.25 | 203.26 | 252.83 | 238.66 | 74.34 | 85.71 |
| Cubic Meters | 1400 | 385.0 | 377.1 | 449.7 | 382.7 | 769.3 | 957.0 | 903.3 | 281.4 | 324.0 |

[a]Contains small amounts of the corresponding olefins.

The principal gaseous streams are calculated to the following compositions in terms of mole percent:

Table II

| | Compositions of Gaseous Streams | | |
|---|---|---|---|
| | Line | | |
| Component | 38 | 39 | 42 |
| Hydrogen | 87.8 | 100 | — |

Table II-continued

| | Compositions of Gaseous Streams | | |
|---|---|---|---|
| | Line | | |
| Component | 38 | 39 | 42 |
| Carbon Dioxide | 3.9 | — | 31.8 |
| Methane | 2.7 | — | 21.9 |
| $C_2$'s | 2.2 | — | 17.7 |
| $C_3$'s | 2.1 | — | 17.1 |
| $C_4$'s | 0.9 | — | 7.1 |
| $C_5$'s | 0.5 | — | 4.4 |
| Volume Per Day | | | |
| Cubic feet Millions[a] | 14.463 | 12.167 | 1.765 |
| Cubic meters thousands[b] | 401.68 | 340.2 | 47.26 |

[a]Calculated at 1 atmosphere (1 bar) and 60° F (16° C).
[b]Calculated at 1 bar and 0° C.

The above example demonstrates the operability of the invention.

Reasonable variations and modifications, which will be apparent to those skilled in the art, can be made in this invention without departing from the spirit and scope thereof.

What is claimed is:

1. A process or producing benzene, cyclohexane and an isohexane concentrate which comprises the steps of:
   a. processing a hydrocarbon-containing feedstock to obtain a first stream consisting essentially of hydrocarbons having six carbon atoms;
   b. fractionating said first stream to obtain a second stream comprising hydrocarbons having a boiling point in the isohexanes range and a third stream comprising hydrocarbons having a boiling point above the isohexanes range;
   c. fractionating said third stream to obtain a fourth stream comprising hydrocarbons boiling in the n-hexane range and a fifth stream comprising hydrocarbons having a boiling point above the n-hexane range;
   d. combining said second stream and said fifth stream to obtain a sixth stream;
   e. hydrogenating said sixth stream to obtain a seventh stream comprising saturated hydrocarbons having six carbon atoms;
   f. isomerizing said seventh stream to obtain an eighth stream comprising isohexanes, cyclohexane and n-hexane;

g. fractionating said eighth stream to obtain an isohexane concentrate and a ninth stream comprising cyclohexane, isohexane and n-hexane;
h. withdrawing said isohexane concentrate as a first product of the process;
i. recovering from said ninth stream a cyclohexane concentrate as a second product of the process;
j. reforming said fourth stream to obtain a tenth reformate stream; and
k. recovering from said reformate stream a benzene concentrate as a third product of the process.

2. The process of claim 1 wherein there is recovered from said ninth stream an eleventh stream comprising n-hexane and isohexane, wherein said eleventh stream is combined with said seventh stream and the resulting combined stream is isomerized.

3. The process of claim 1 wherein said cyclohexane concentrate is further fractionated to obtain a product stream consisting essentially of cyclohexane.

4. The process of claim 1 wherein said reformate stream is fractionated to obtain said benzene concentrate, a twelfth stream consisting of hydrogen and a thirteenth stream comprising methane and wherein at least a portion of said twelfth stream is passed to and combined with said sixth stream.

5. The process of claim 4 wherein said benzene concentrate is further treated to obtain a product stream consisting essentially of benzene and a fourteenth stream comprising n-hexane and isohexane.

6. The process of claim 5 wherein said fourteenth stream is combined with said first stream.

7. The process of claim 1 wherein said fourth stream is reformed in a reforming zone under reforming conditions in the presence of steam and in the presence of a reforming catalyst selected from the group consisting of at least one Group VIII metal in combination with a tin-modified Group II metal aluminate.

8. The process of claim 7 wherein said Group VIII metal is selected from the group consisting of nickel, platinum, palladium, iridium, osmium and mixtures thereof.

9. The process of claim 8 wherein said Group VIII metal is platinum

10. The process of claim 7 wherein said Group VII metal aluminate is zinc aluminate.

* * * * *